US00PP28197P3

(12) United States Plant Patent
Tanjga

(10) Patent No.: US PP28,197 P3
(45) Date of Patent: Jul. 18, 2017

(54) ***ROSA* PLANT NAMED 'BOZMILLWIN '**

(50) Latin Name: *Rosa hybrida*
Varietal Denomination: BOZMILLWIN

(71) Applicant: Biljana Bozanic Tanjga, Novi Sad (RS)

(72) Inventor: Biljana Bozanic Tanjga, Novi Sad (RS)

( * ) Notice: Subject to any disclaimer, the term of this patent is extended or adjusted under 35 U.S.C. 154(b) by 0 days.

(21) Appl. No.: 14/756,338

(22) Filed: Aug. 27, 2015

(65) Prior Publication Data

US 2017/0064887 P1 Mar. 2, 2017

(51) Int. Cl.
*A01H 5/02* (2006.01)

(52) U.S. Cl.
USPC ..... Plt./103

(58) Field of Classification Search
USPC ..... Plt./103
CPC ..... A01H 5/0222
See application file for complete search history.

(56) References Cited

PUBLICATIONS http://www.newplantsandflowers.com/long-blooming-vigorous-and-hardy-rose-from-serbia/; Aug. 20, 2014; 1 page.*

* cited by examiner

*Primary Examiner* — Kent L Bell
(74) *Attorney, Agent, or Firm* — Cassandra Bright

(57) ABSTRACT

A new and distinct *Rosa* cultivar named 'BOZMILLWIN' is disclosed, characterized by pure white flower petals, winter hardiness, very upright branching, leathery, shiny leaves and resistance to powdery mildew and black spot. The new variety is a *Rosa*, normally produced as an outdoor garden or container plant.

4 Drawing Sheets

Latin name of the genus and species: *Rosa hybrida.*
Variety denomination: 'BOZMILLWIN'.

BACKGROUND OF THE INVENTION

The new *Rosa* cultivar is a product of a planned breeding program conducted by the inventor, Biljana Bozanic Tanjga, in Mali Idjos, Serbia. The objective of the breeding program was to produce new *Rosa* varieties for ornamental commercial applications. The cross resulting in this new variety was made during June of 2009.

The seed parent is *Rosa* 'Pouldiram', U.S. Plant Pat. No. 12,568. The pollen parent is the unpatented, commercial variety *Rosa* 'Adelaide Hoodless'. The new variety was discovered in April of 2010 by the inventor in a group of seedlings resulting from the 2009 crossing, in a research nursery in Mali Idjos, Serbia Asexual reproduction of the new cultivar was performed by grafting a bud of the new variety onto rootstock *Rosa corymbifera* 'Laxa'. This was first performed at a research nursery in Mali Idjos, Serbia in April of 2010 and has shown that the unique features of this cultivar are stable and reproduced true to type in multiple successive generations.

SUMMARY OF THE INVENTION

The cultivar 'BOZMILLWIN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BOZMILLWIN'. These characteristics in combination distinguish 'BOZMILLWIN' as a new and distinct *Rosa* cultivar:

1. Pure white petal color.
2. Winter hardy to at least USDA Zone 2.
3. Very upright branching habit.
4. Leathery, shiny leaves.
5. Resistant to powdery mildew and black spot.

Plants of the new cultivar 'BOZMILLWIN' are similar to plants of the seed parent in most horticultural characteristics, however, plants of the new cultivar 'BOZMILLWIN' differ in the following;

1. Shorter plant than the seed parent.
2. Larger flowers with more petals than the seed parent.
3. Later blooming than the seed parent.
4. White flowers, whereas the parent has cream colored shading on the flower petals.
5. Darker green foliage.

Plants of the new cultivar 'BOZMILLWIN' are similar to plants of the pollen parent in most horticultural characteristics, however, plants of the new cultivar 'BOZMILLWIN' differ in the following;

1. White flowers, whereas the parent has deep pink flower color.
2. Less bushy in form.
3. Parent has presence of anthocyanin in young leaves and branches. This is not present in the new variety.
4. Less petals per flower than the pollen parent.
5. Shorter in height than the pollen parent.

COMMERCIAL COMPARISON

Plants of the new cultivar 'BOZMILLWIN' are comparable to the patented commercial variety *Rosa* 'Flower Carpet White', U.S. Plant Pat. No. 9,573. The two *Rosa* varieties are similar in most horticultural characteristics; however, the new variety 'BOZMILLWIN' differs in the following:

1. The new variety has a flat flower form, while the comparator has a more cupped flower form.
2. The new variety has less petals per flower than the comparator.
3. Smaller flower size than the comparator.
4. Less fragrance than the comparator.
5. Lighter colored anthers than the comparator.

Plants of the new cultivar 'BOZMILLWIN' are also comparable to the unpatented commercial variety *Rosa* 'Sheer Silk'. The two *Rosa* varieties are similar in most horticultural characteristics; however, the new variety 'BOZMILLWIN' differs in the following:

1. The new variety has less ruffled flowers than the comparator.
2. The comparator has smoother branches.
3. The new variety has darker green leaves.
4. The new variety is more upright in growth, while the comparator is of spreading growth habit.
5. The new variety has smaller flowers than the comparator.

BRIEF DESCRIPTION OF THE PHOTOGRAPHS

The accompanying photograph in FIG. 1 illustrates in full color a typical plant of 'BOZMILLWIN' grown in the ground. Age of the plant photographed is approximately 5 months.

Figure 1:
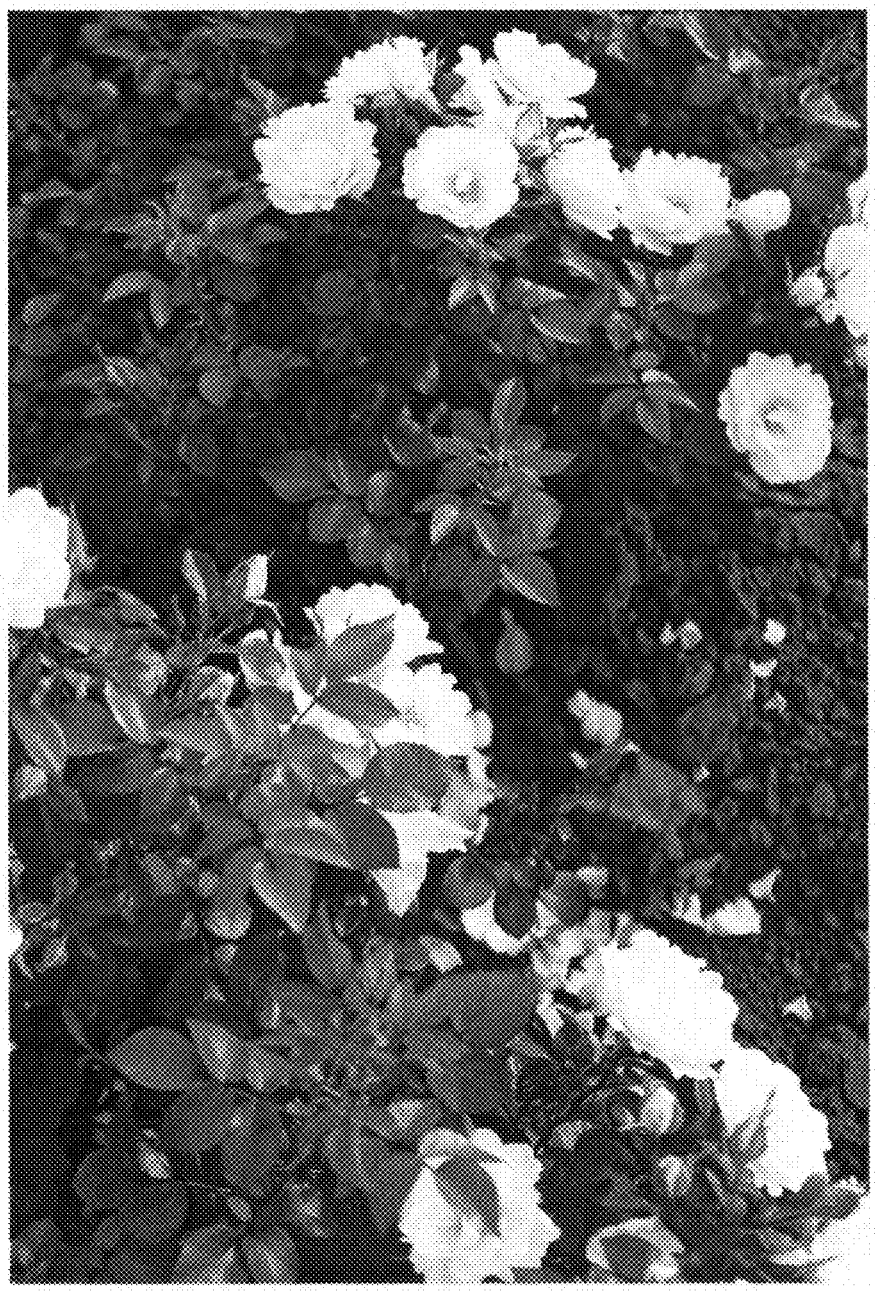
Figure 2:
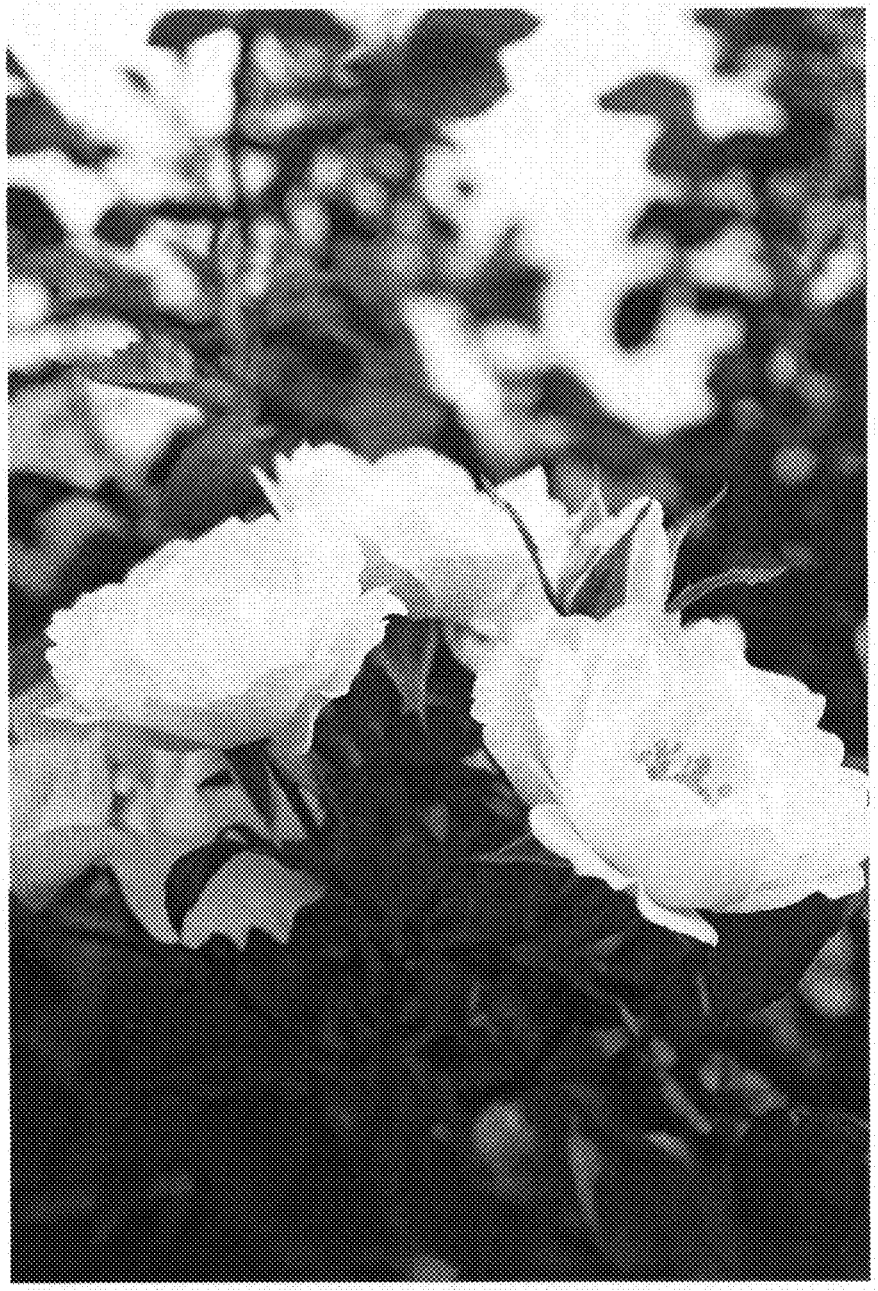
FIG. 2 and FIG. 3 illustrate multiple flowers.
Figure 3:
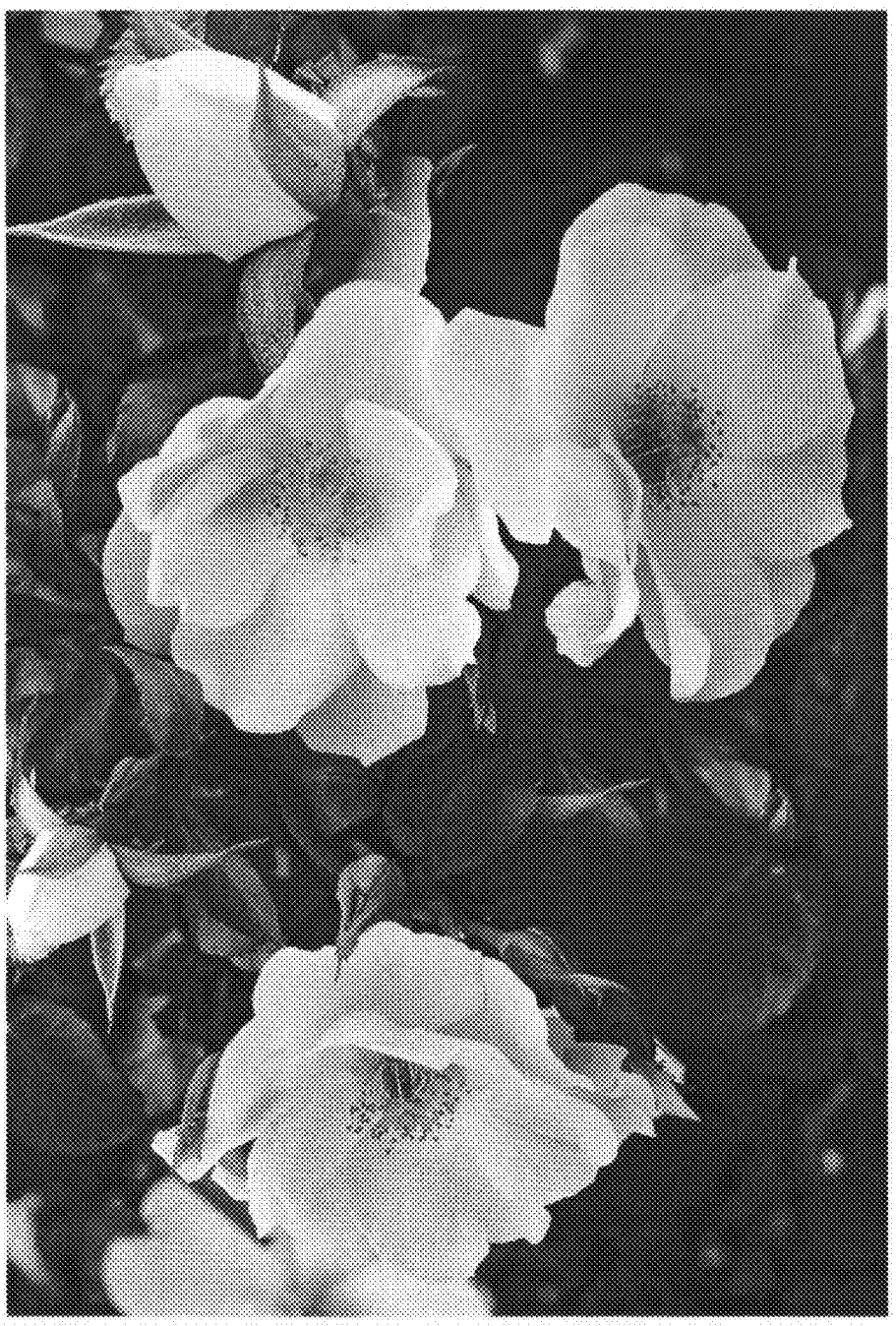
Figure 4:
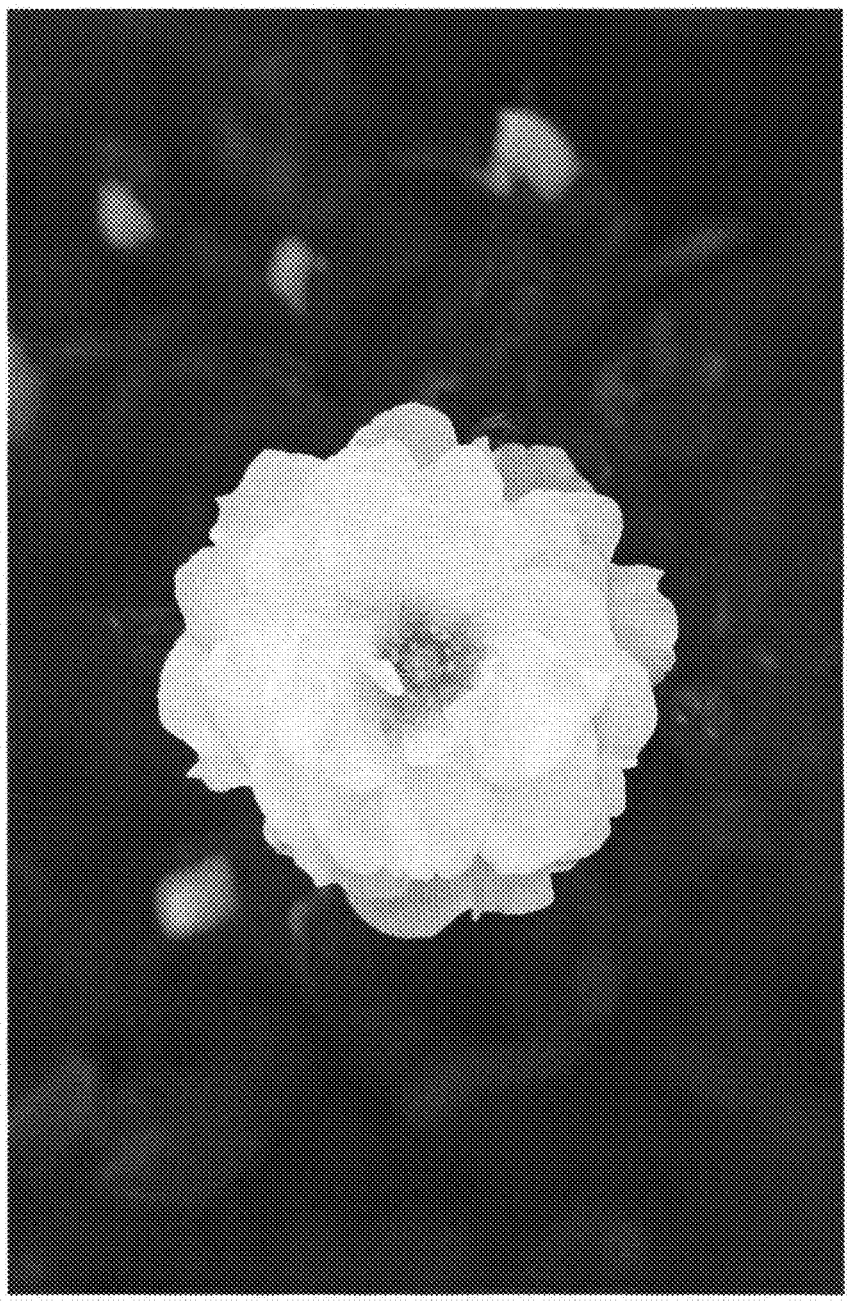
FIG. 4 illustrates a single flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BOZMILLWIN' plants grown outdoors during the Spring and Summer, in Temerin, Serbia. The growing temperature ranged from −15° C. to +40° C. during the day and from −25° C. to +30° C. during the night. General light conditions were bright, normal sunlight. No chemical treatments were used. Measurements and numerical values represent averages of typical plant types.

Botanical classification: *Rosa* 'BOZMILLWIN'.

PROPAGATION

Root description: Propagation by budding onto rootstock *Rosa corymbifera* 'Laxa'.

PLANT

Age of plant described: Approximately 2 years old.
Growth habit: Semi-upright shrub.
Planting condition of described plant: Planted in soil.
Rootstock: *R. corymbifera* 'Laza'.
Height: Up to 60 cm.
Plant spread: Approximately 80 cm.
Growth rate: Approximately 1 year to reach 0.6 meters.
Branching characteristics: Semi-upright.
Length of primary lateral branches: Approximately 30-60 cm.
Diameter of lateral branches: Approximately 0.5 cm.
Quantity of lateral branches: Average 10.
Branches — young wood:
*Diameter*.—Approximately 0.4 cm.
*Texture*.—Smooth.
*Approximately density/quantity of thorns*.—10-13 per 10 cm of length.
*Color*.—Near RHS Green 143C.
Branches — old wood:
*Diameter*.—Approximately 0.8 cm, after 1 year.
*Texture*.—Slightly fissured branches.
*Approximately density/quantity of thorns*.—6-7 per 5 cm of length.
*Color*.—Near RHS Yellow-green 146B.

FOLIAGE

Leaf:
*Arrangement*.—Spiral.
*Quantity*.—Approximately 3 occurring per 10 cm of length per main branch.
*Average length*.—Approximately 9 cm.
*Average width*.—Approximately 5.5 cm.
Leaflet:
*Quantity*.—Approximately 5-7 per leaf.
*Average length*.—Approximately 3 cm.
*Average width*.—Approximately 2 cm.
*Shape of blade*.—Apex: Cuspidate. Base: rounded (obtuse). Margin: Serrate.
*Texture of top surface*.—Leathery (smooth and shiny).
*Texture of bottom surface*.—Glabrous, leathery, mat.
*Pubescence*.—No hairs.
*Leaf internode length*.—1.1 cm.
*Color*.—Young foliage upper side: Near RHS Green 137A. Young foliage under side: Near RHS Yellow-green 146B. Mature foliage upper side: Near RHS Yellow-green 147A. Mature foliage under side: Near RHS Yellow-green 147B.
*Venation*.—Type: Pinnate. Venation color upper side: Near RHS Yellow-Green 144C. Venation color under side: Near the same as under side leaflet coloration (near RHS Yellow-green 147B).
*Petiole*.—Length: 0.7 cm. Width: 0.5 cm. Color: Young foliage near RHS Greyed-Red 181 A, mature foliage near Yellow-Green N144B, flushed 181A. Texture: With small thorns.

FLOWER

Natural flowering season: End of May until end of September.
Begins flowering after how many years/months: In the same year after budding (in 1$^{st}$ year).
Flower type and habit: Semi-double, with a flat aspect.
Rate of flower opening: Approximately 5 days from bud to fully opened flower.
Flower longevity on plant: 8 days, after fully opened.
Quantity of flowers: 15-23 per branch.
Inflorescence size:
*Diameter*.—Approximately 6-8 cm.
*Length*.—Approximately 12 cm.

Peduncle:
*Length.*—1.5-2 cm.
*Diameter.*—0.2 cm.
*Color.*—Near RHS Yellow-Green 146C, heavily or entirely flushed Greyed-Purple 183D.

Petals:
*Petal arrangement.*—Semi double flower, round flower with flat profile of upper part and flat profile of lower part.
*Size.*—Length: 2.9 cm. Width: 2.5 cm.
*Shape.*—Rounded.
*Margin.*—Entire and very slightly ruffled.
*Apex.*—Obtuse with 1 to 3 irregular, rounded notches.
*Base.*—Obtuse, rounded.
*Petal quantity.*—15-18.
*Texture.*—Silky and smooth.

Color:
Petals:
*When opening.*—Upper surface: Near RHS Orange-white 159D. Lower surface: Near RHS Orange-white 159B.
*Fully opened.*—Upper surface: Near RHS White 155B. Lower surface: Near RHS White 155D. Color Changes when aging: no.

Bud:
*Shape.*—Conical.
*Length.*—Approximately 2 cm.
*Diameter.*—Approximately 1 cm.
*Color.*—Near RHS Yellow-green 144B.

Sepals:
*Length.*—2.2-2.5 cm.
*Width.*—0.6 cm.
*Shape.*—Narrow deltate with weak extensions.
*Color.*—Interior Surface: RHS Yellow-green 148C. Exterior Surface: RHS Yellow-green 146B.
*Texture.*—Hairy.

Receptacle:
*Length.*—0.9 cm.
*Width.*—0.5 cm.
*Shape.*—Cylindrical shape.
*Color.*—Near RHS Green 137C.

Fragrance: Slightly fragrant.

REPRODUCTIVE ORGANS

Stamens:
*Number.*—Variable, 150 to 400.
*Filament length.*—Approximately 0.4-1 cm.
*Filament color.*—Yellow.

Anthers:
*Length.*—2 mm×1 mm.
*Shape.*—Oval.
*Color.*—Near RHS Greyed-orange 163B.
*Pollen.*—Color: Near RHS Yellow-orange 17A. Quantity: Good amount of pollen.

Pistil:
*Number.*—50.
*Length.*—Approximately 4 mm.
*Style.*—Length: Approximately 0.3 cm. Color: Near RHS Yellow-green 144D.
*Stigma.*—Shape: Four parts. Color: Near RHS Greyed-orange 164C. Ovary Color: Near RHS Green 142C.

OTHER CHARACTERISTICS

Seeds and fruits: Medium orange color, rounded shape.
Disease/pest resistance: Resistant to powdery mildew.
Temperature tolerance: −25° C. up to +40° C. degrees.

What is claimed is:

1. A new and distinct cultivar of *Rosa* plant named 'BOZMILLWIN' as herein illustrated and described.

* * * * *